United States Patent
Kazanjian et al.

(10) Patent No.: US 6,755,085 B1
(45) Date of Patent: Jun. 29, 2004

(54) GOLF BALL TESTING APPARATUS

(76) Inventors: Harry Kazanjian, 35330 Lone Pine La., Farmington Hills, MI (US) 48335; Margaret Kazanjian, 35330 Lone Pine La., Farmington Hills, MI (US) 48335

( * ) Notice: Subject to any disclaimer, the term of this patent is extended or adjusted under 35 U.S.C. 154(b) by 0 days.

(21) Appl. No.: 10/158,949

(22) Filed: May 31, 2002

(51) Int. Cl.[7] ................................ G01N 3/08
(52) U.S. Cl. ................................ 73/824
(58) Field of Search .............. 209/599; 73/65.02, 73/81, 818, 824, 12.01, 12.14, 12.02; 194/240; 29/714; 273/317.1

(56) References Cited

U.S. PATENT DOCUMENTS

| | | |
|---|---|---|
| 1,819,232 A | 8/1931 | Cropper |
| 2,278,416 A | 4/1942 | Atti |
| 2,628,496 A | 2/1953 | Wick |
| 3,665,757 A | 5/1972 | Hoag |
| 4,509,362 A | 4/1985 | Lyons |
| 4,555,028 A | 11/1985 | Valehrach |
| 5,222,391 A * | 6/1993 | Reenstra ................ 73/81 |
| D347,394 S | 5/1994 | Schlesinger et al. |
| 5,511,410 A * | 4/1996 | Sherts ................ 73/81 |
| 5,639,969 A * | 6/1997 | D'Adamo ............ 73/818 |
| 5,760,312 A * | 6/1998 | Mackay et al. ....... 73/818 |
| 6,196,073 B1 * | 3/2001 | Harding ........... 73/862.381 |

* cited by examiner

*Primary Examiner*—Edward Lefkowitz
*Assistant Examiner*—Octavia Davis

(57) ABSTRACT

A golf ball testing apparatus for testing whether a golf ball is usable for competitive use. The golf ball testing apparatus includes a housing having a perimeter wall. The perimeter wall of the housing defines a orifice through the housing. The orifice is designed for receiving the golf ball. A plurality of alignment assemblies are coupled to the housing. Each of the alignment assemblies is designed for abutting against the golf ball for maintaining alignment of the golf ball in the orifice. A compression assembly is coupled to the housing. The compression assembly is designed for engaging the golf ball. A measurement assembly is coupled to the housing opposite the compression assembly. The measurement assembly is designed for engaging the golf ball for measuring compression of the golf ball when the compression assembly compresses the golf ball.

13 Claims, 4 Drawing Sheets

GOLF BALL TESTING APPARATUS

BACKGROUND OF THE INVENTION

1. Field of the Invention

The present invention relates to portable golf ball testers and more particularly pertains to a new golf ball testing apparatus for testing whether a golf ball is usable for competitive use.

2. Description of the Prior Art

The use of portable golf ball testers is known in the prior art. U.S. Pat. No. 2,628,496 describes a device for testing the compressible resiliency of golf balls. Another type of portable golf ball tester is U.S. Pat. No. 1,819,232 having an instrument for receiving a ball and testing the compressible nature of the ball being tested. U.S. Pat. No. 2,278,416 has a machine for receiving and testing the compressible nature of a golf ball. U.S. Pat. No. 4,555,028 has an apparatus for testing golf balls under compression and sorting the golf balls according to their compression ratings. U.S. Pat. No. 4,509,362 has a device for testing the resilience of a game ball. U.S. Pat. No. 3,665,757 has a gauge for testing the concentricity and compressibility of a golf ball. U.S. Pat. No. Des. 347,394 shows a golf ball tester.

While these devices fulfill their respective, particular objectives and requirements, the need remains for a device that has certain improved features for maintaining the alignment of the golf ball while the golf ball is being tested.

SUMMARY OF THE INVENTION

The present invention meets the needs presented above by providing a plurality of alignment assemblies coupled to the housing that engage a golf ball placed in the orifice of the housing for maintaining the alignment of the golf ball when the golf ball is being tested.

Still yet another object of the present invention is to provide a new golf ball testing apparatus that allows a user to test whether a golf ball is substantially spherical and has an acceptable compressibility.

To this end, the present invention generally comprises a housing having a perimeter wall. The perimeter wall of the housing defines a orifice through the housing. The orifice is designed for receiving the golf ball. A plurality of alignment assemblies are coupled to the housing. Each of the alignment assemblies extends through the perimeter wall of the housing. Each of the alignment assemblies is designed for abutting against the golf ball for maintaining alignment of the golf ball when the golf ball is positioned in the orifice of the housing. A compression assembly is coupled to the housing. The compression assembly extends into the orifice of the housing. The compression assembly is designed for engaging the golf ball when the golf ball is positioned in the orifice of the housing. A measurement assembly is coupled to the housing opposite the compression assembly. The measurement assembly extends into the orifice of the housing. The measurement assembly is designed for engaging the golf ball when the golf ball is positioned in the orifice of the housing for measuring compression of the golf ball when the compression assembly compresses the golf ball.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
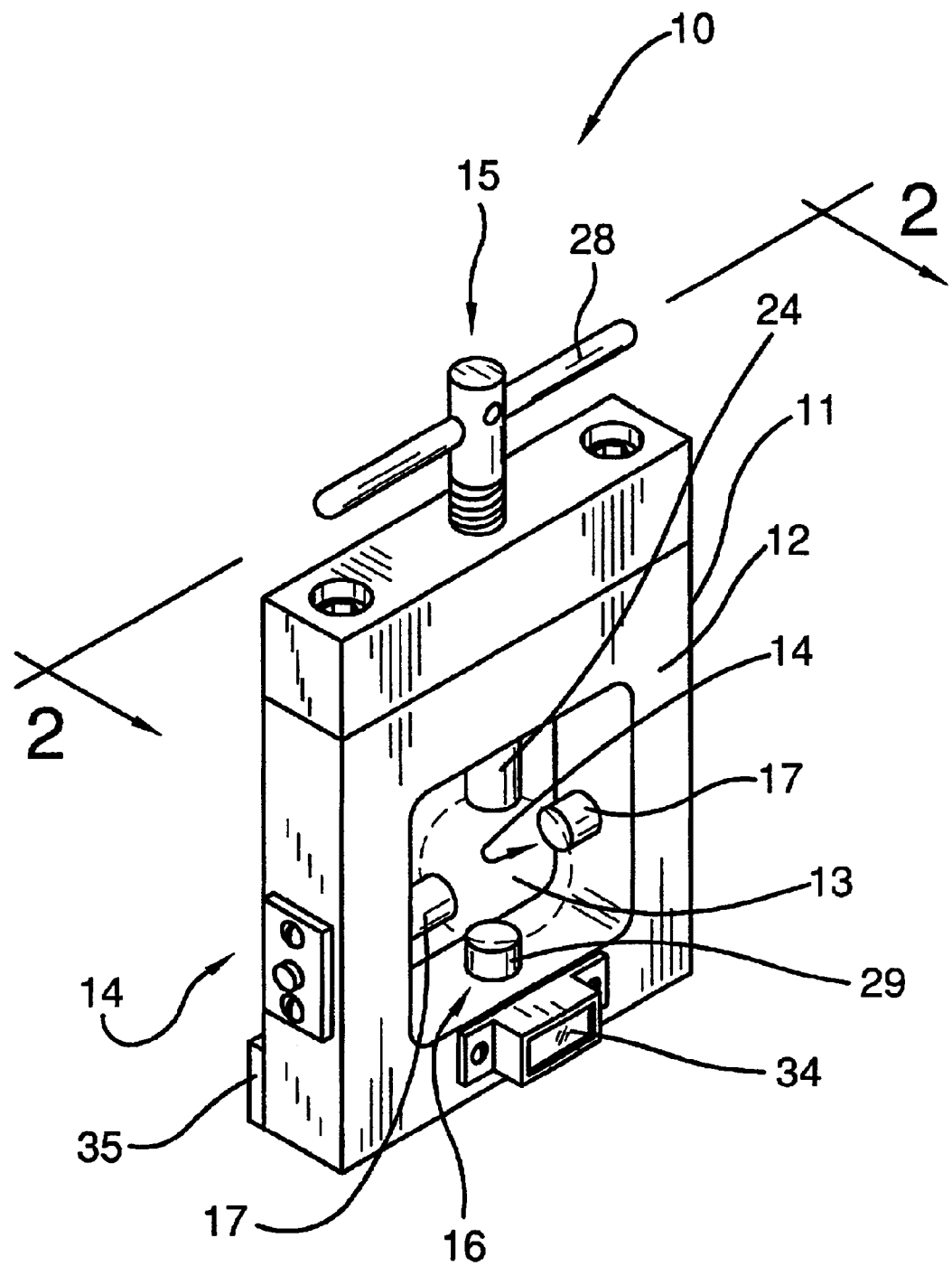
FIG. 1 is a front perspective view of a new golf ball testing apparatus according to the present invention.
Figure 2:
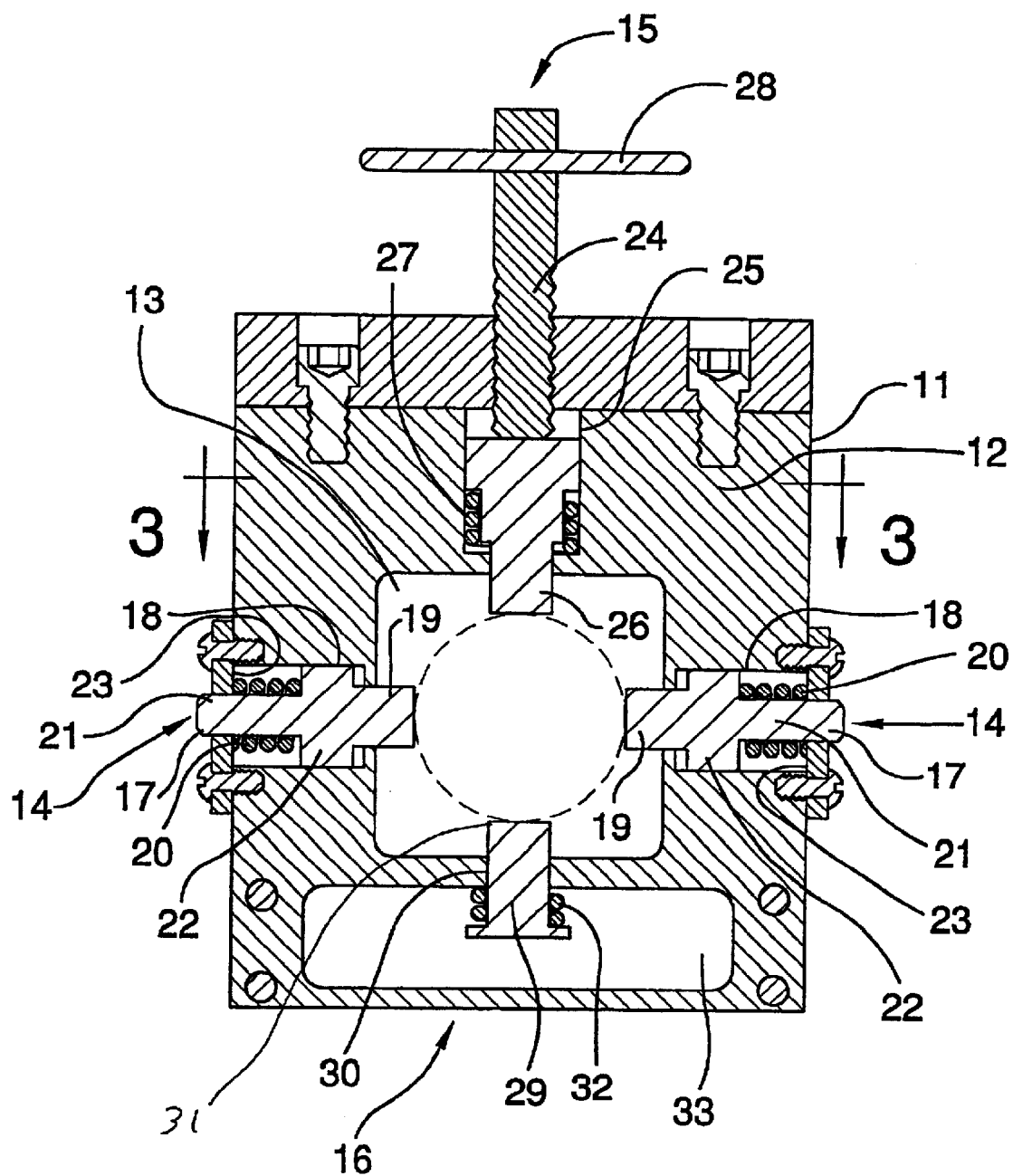
FIG. 2 is a cross-sectional view of the present invention taken along line 2—2 of FIG. 1.
Figure 5:
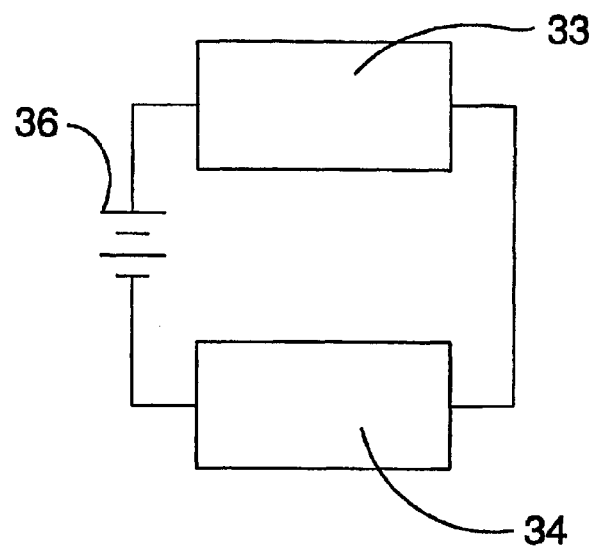
FIG. 5 is a schematic view of the display member, scale means and power supply of the present invention.
Figure 3:
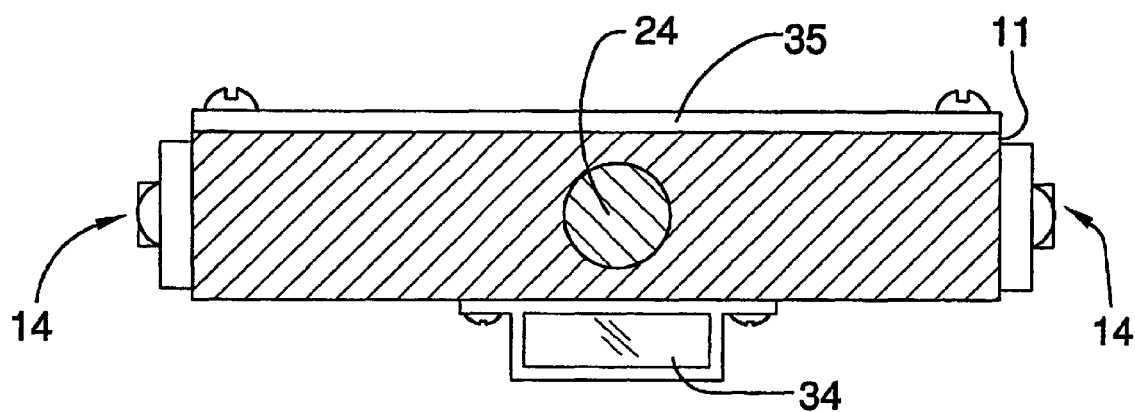
FIG. 3 is a cross-sectional view of the present invention taken along line 3—3 of FIG. 2.
Figure 4:
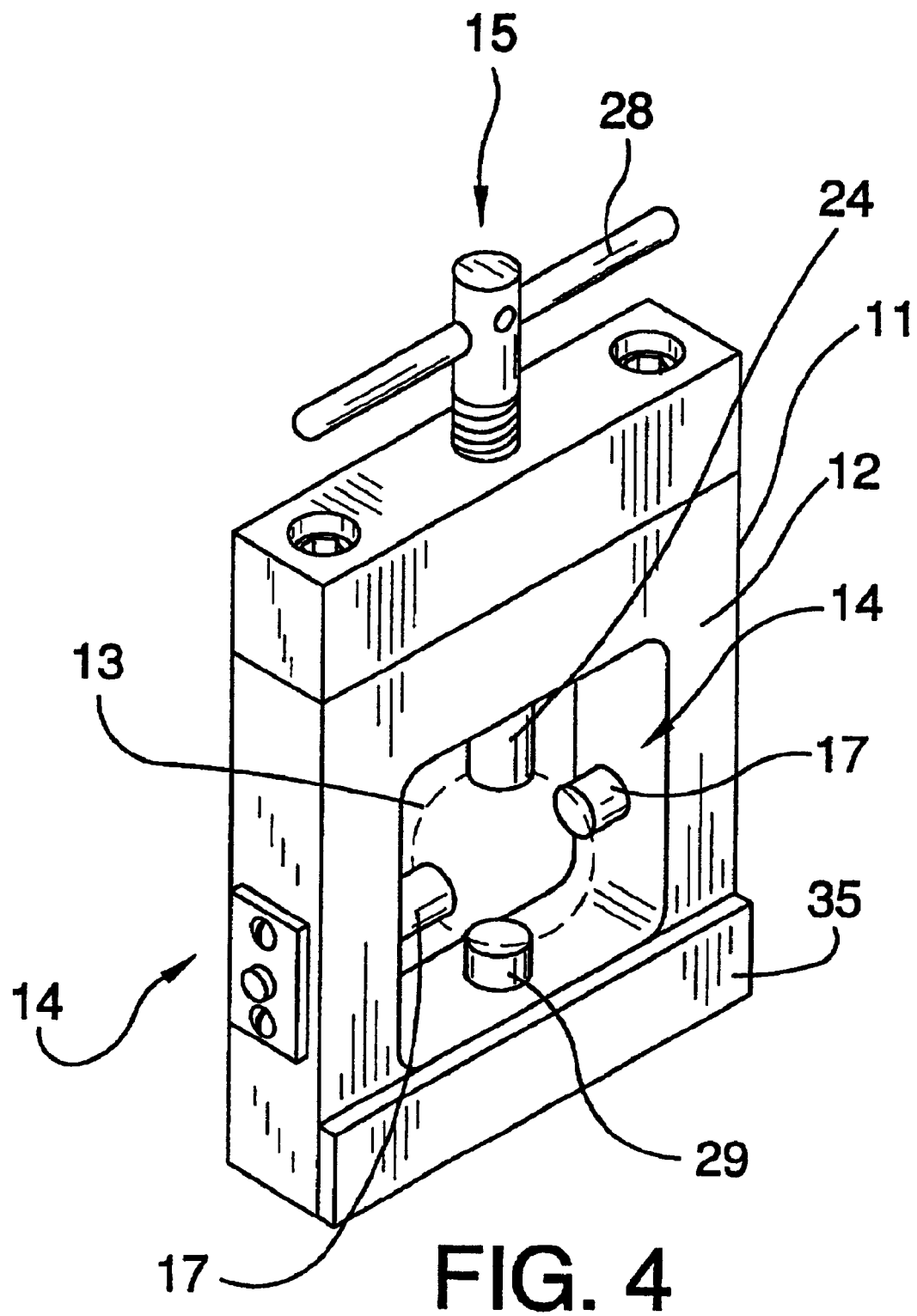
FIG. 4 is a rear perspective view of the present invention.

With reference now to the drawings, and in particular to FIGS. 1 through 5 thereof, a new golf ball testing apparatus embodying the principles and concepts of the present invention and generally designated by the reference numeral 10 will be described.

As best illustrated in FIGS. 1 through 5, the golf ball testing apparatus 10 generally comprises a housing 11 having a perimeter wall 12. The perimeter wall 12 of the housing 11 defines a orifice 13 through the housing 11. The orifice 13 is designed for receiving the golf ball.

A plurality of alignment assemblies 14 are coupled to the housing 11. Each of the alignment assemblies 14 extends through the perimeter wall 12 of the housing 11. Each of the alignment assemblies 14 is designed for abutting against the golf ball for maintaining alignment of the golf ball when the golf ball is positioned in the orifice 13 of the housing 11.

A compression assembly 15 is coupled to the housing 11. The compression assembly 15 extends into the orifice 13 of the housing 11. The compression assembly 15 is designed for engaging the golf ball when the golf ball is positioned in the orifice 13 of the housing 11.

A measurement assembly 16 is coupled to the housing 11 opposite the compression assembly 15. The measurement assembly 16 extends into the orifice 13 of the housing 11. The measurement assembly 16 is designed for engaging the golf ball when the golf ball is positioned in the orifice 13 of the housing 11 for measuring compression of the golf ball when the compression assembly 15 compresses the golf ball.

Each of the alignment assemblies 14 comprises an alignment rod 17. The alignment rod 17 extends through one of a plurality of alignment apertures 18 extending through the perimeter wall 12 of the housing 11. A free end 19 of the alignment rod 17 of each of the alignment assemblies 14 is designed for engaging the golf ball when the golf ball is positioned in the orifice 13 of the housing 11.

Each of the alignment assemblies 14 comprises an alignment biasing member 20. The alignment biasing member 20 is positioned between the housing 11 and the alignment rod 17 of the associated one of the alignment assemblies 14. The alignment biasing member 20 biases the free end 19 of the alignment rod 17 of the associated one of the alignment assemblies 14 into the orifice 13 of the housing 11.

The alignment rod 17 of each of the alignment assemblies 14 comprises a main portion 21 and a lip portion 22. The lip portion 22 has a diameter greater than the main portion 21 of the alignment rod 17 of the associated one of the alignment assemblies 14 whereby the alignment biasing member 20 is positioned between the lip portion 22 and an alignment ledge 23 of the associated one of the alignment apertures 18 of the housing 11.

The compression assembly 15 comprises a compression rod 24. The compression rod 24 extends through a compression aperture 25 of the housing 11 whereby an engaging end 26 of the compression rod 24 is positioned in the orifice 13 of the housing 11. The engaging end 26 is designed for engaging the golf ball when the golf ball is positioned in the orifice 13 of the housing 11. The compression rod 24 of the compression assembly 15 is threadably coupled to the housing 11 whereby pressure of the engaging end 26 of the compression rod 24 against the golf ball is adjustable when the compression rod 24 is rotated with respect to the housing 11.

The compression assembly 15 comprises a compression biasing member 27. The compression biasing member 27 is positioned between the housing 11 and the compression rod 24 whereby the compression biasing member 27 biases the engaging end 26 of the compression rod 24 away from the golf ball when the compression rod 24 is rotated to relieve pressure from the golf ball.

The compression assembly 15 comprises a handle bar 28. The handle bar 28 is coupled to the compression rod 24 opposite the engaging end 26 of the compression rod 24. The handle bar 28 is designed for being griped by the user for rotating the compression rod 24.

The measuring assembly comprises a measuring rod 29. The measuring rod 29 extends through a measuring aperture 30 of the housing 11 whereby a distal end 31 of the measuring rod 29 is positioned in the orifice 13 of the housing 11. The distal end 31 of the measuring rod 29 is designed for engaging the golf ball when the golf ball is positioned in the orifice 13 of the housing 11.

The measuring assembly comprises a measuring biasing member 32. The measuring biasing member 32 is positioned between the housing 11 and the measuring rod 29. The measuring biasing member 32 is for biasing the distal end 31 of the measuring rod 29 away from the orifice 13 of the housing 11.

The measuring assembly comprises a scale means 33 for measuring an amount of pressure applied to the golf ball by the compression assembly 15. The scale means 33 is operationally coupled to the measuring rod 29 opposite the distal end 31 of the measuring rod 29 whereby the scale means 33 detects the amount of movement of the measuring rod 29 when the golf ball is being compressed by the compression assembly 15.

A display member 34 is coupled to the housing 11. The display member 34 is operationally coupled to the scale means 33. The display member 34 is for displaying the pressure the golf ball is applying to the measuring rod 29.

A cover plate 35 is selectively coupled to the housing 11. The cover plate 35 covers a power supply 36 positioned within the housing 11 such that the cover plate 35 is removable for replacing the power supply 36. The power supply 36 is operationally coupled to the scale means 33 and the display member 34 for supplying power to the scale means 33 and the display member 34.

In use, the user places a new golf ball in the orifice 13 of the housing 11 so that the golf ball is positioned between the alignment rod 17s, the compression rod 24 and the measuring rod 29. The compression rod 24 is the rotated until the engaging end 26 of the compression rod 24 just contacts the new golf ball. The new golf ball is then rotated within the orifice 13 to determine the true spherical nature of the new golf ball. The compression rod 24 is then rotated until the compression rod 24 will not turn anymore thereby putting the new golf ball in compression. The display is then read to determine a poundage rating for the new golf ball and the new golf ball is removed from the orifice 13 of the housing 11. The user then places a used golf ball of the same type into the orifice 13 and repeats the procedure for the used golf ball. The used golf ball is removed from being a competitive golf ball if the used golf ball is found to be out of round or has poundage rating greater than ten pounds less than or greater than the poundage rating of the new golf ball.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A golf ball testing apparatus for testing the usability of a used golf ball, the golf ball testing apparatus comprising:

a housing having a perimeter wall, said perimeter wall of said housing defining a orifice through said housing such that said orifice extends through a front face and through a rear face of said housing, said orifice being adapted for receiving the golf ball such that said orifice permits the golf ball to be inserted into the orifice through the front of said housing and the rear of said housing;

a plurality of alignment assemblies being coupled to said housing, each of said alignment assemblies extending through said perimeter wall of said housing, each of said alignment members being positioned on opposite sides of said housing, each of said alignment assemblies being adapted for abutting against the golf ball from opposite sides of the golf ball for maintaining alignment of the golf ball when the golf ball is positioned in said orifice of said housing;

a compression assembly being coupled to said housing, said compression assembly extending into said orifice of said housing, said compression assembly being adapted for engaging the golf ball when the golf ball is positioned in said orifice of said housing; and a measurement assembly being coupled to said housing opposite said compression assembly, said measurement assembly extending into said orifice of said housing, said measurement assembly being adapted for engaging the golf ball when the golf ball is positioned in said orifice of said housing for measuring compression of the golf ball when said compression assembly compresses the golf ball.

2. The golf ball testing apparatus as set forth in claim 1, further comprising:

each of said alignment assemblies comprising an alignment rod, said alignment rod extending through one of a plurality of alignment apertures extending through said perimeter wall of said housing, a free end of said alignment rod of each of said alignment assemblies being adapted for engaging the golf ball when the golf ball is positioned in said orifice of said housing.

3. The golf ball testing apparatus as set forth in claim 2, further comprising:

each of said alignment assemblies comprising an alignment biasing member, said alignment biasing member being positioned between said housing and said alignment rod of the associated one of said alignment assemblies, said alignment biasing member biasing said free end of said alignment rod of the associated one of said alignment assemblies into said orifice of said housing.

4. The golf ball testing apparatus as set forth in claim 3, further comprising:

said alignment rod of each of said alignment assemblies comprising a main portion and a lip portion, said lip portion having a diameter greater than said main portion of said alignment rod of the associated one of said alignment assemblies such that said alignment biasing member is positioned between said lip portion and an alignment ledge of the associated one of said alignment apertures of said housing.

5. The golf ball testing apparatus as set forth in claim 1, further comprising:

said compression assembly comprising a compression rod, said compression rod extending through a compression aperture of said housing such that an engaging end of said compression rod is positioned in said orifice of said housing, said engaging end being adapted for engaging the golf ball when the golf ball is positioned in said orifice of said housing.

6. The golf ball testing apparatus as set forth in claim 5, wherein said compression rod of said compression assembly is threadably coupled to said housing such that pressure of said engaging end of said compression rod against the golf ball is adjustable when said compression rod is rotated with respect to said housing.

7. The golf ball testing apparatus as set forth in claim 6, further comprising:

said compression assembly comprising a compression biasing member, said compression biasing member being positioned between said housing and said compression rod such that said compression biasing member biases said engaging end of said compression rod away from the golf ball when said compression rod is rotated to relieve pressure from the golf ball.

8. The golf ball testing apparatus as set forth in claim 6, further comprising:

said compression assembly comprising a handle bar, said handle bar being coupled to said compression rod opposite said engaging end of said compression rod, said handle bar being adapted for being griped by the user for rotating said compression rod.

9. The golf ball testing apparatus as set forth in claim 1, further comprising:

said measuring assembly comprising a measuring rod, said measuring rod extending through a measuring aperture of said housing such that a distal end of said measuring rod is positioned in said orifice of said housing, said distal end of said measuring rod being adapted for engaging the golf ball when the golf ball is positioned in said orifice of said housing.

10. The golf ball testing apparatus as set forth in claim 9, further comprising:

said measuring assembly comprising a measuring biasing member, said measuring biasing member being positioned between said housing and said measuring rod, said measuring biasing member being for biasing said distal end of said measuring rod away from said orifice of said housing.

11. The golf ball testing apparatus as set forth in claim 9, further comprising:

said measuring assembly comprising a scale means for measuring an amount of pressure applied to the golf ball by said compression assembly, said scale means being operationally coupled to said measuring rod opposite said distal end of said measuring rod such that said scale means detects the amount of movement of said measuring rod when the golf ball is being compressed by said compression assembly.

12. The golf ball testing apparatus as set forth in claim 11, further comprising:

a display member being coupled to said housing, said display member being operationally coupled to said scale means, said display member being for displaying the pressure the golf ball is applying to said measuring rod.

13. A golf ball testing apparatus for testing the usability of a used golf ball, the golf ball testing apparatus comprising:

a housing having a perimeter wall, said perimeter wall of said housing defining a orifice through said housing such that said orifice extends through a front face and through a rear face of said housing, said orifice being adapted for receiving the golf ball such that said orifice permits the golf ball to be inserted into the orifice through the front of said housing and the rear of said housing;

a plurality of alignment assemblies being coupled to said housing, each of said alignment assemblies extending through said perimeter wall of said housing, each of said alignment members being positioned on opposite sides of said housing, each of said alignment assemblies being adapted for abutting against the golf ball from opposites side of the golf ball for maintaining alignment of the golf ball when the golf ball is positioned in said orifice of said housing;

a compression assembly being coupled to said housing, said compression assembly extending into said orifice of said housing, said compression assembly being adapted for engaging the golf ball when the golf ball is positioned in said orifice of said housing;

a measurement assembly being coupled to said housing opposite said compression assembly, said measurement assembly extending into said orifice of said housing, said measurement assembly being adapted for engaging the golf ball when the golf ball is positioned in said orifice of said housing for measuring compression of the golf ball when said compression assembly compresses the golf ball;

each of said alignment assemblies comprising an alignment rod, said alignment rod extending through one of a plurality of alignment apertures extending through said perimeter wall of said housing, a free end of said alignment rod of each of said alignment assemblies being adapted for engaging the golf ball when the golf ball is positioned in said orifice of said housing;

each of said alignment assemblies comprising an alignment biasing member, said alignment biasing member being positioned between said housing and said alignment rod of the associated one of said alignment assemblies, said alignment biasing member biasing said free end of said alignment rod of the associated one of said alignment assemblies into said orifice of said housing;

said alignment rod of each of said alignment assemblies comprising a main portion and a lip portion, said lip portion having a diameter greater than said main portion of said alignment rod of the associated one of said alignment assemblies such that said alignment biasing member being positioned between said lip portion and an alignment ledge of the associated one of said alignment apertures of said housing;

said compression assembly comprising a compression rod, said compression rod extending through a compression aperture of said housing such that an engaging end of said compression rod is positioned in said orifice of said housing, said engaging end being adapted for engaging the golf ball when the golf ball is positioned in said orifice of said housing;

said compression rod of said compression assembly being threadably coupled to said housing such that pressure of said engaging end of said compression rod against the golf ball is adjustable when said compression rod is rotated with respect to said housing;

said compression assembly comprising a compression biasing member, said compression biasing member being positioned between said housing and said compression rod such that said compression biasing member biases said engaging end of said compression rod away from the golf ball when said compression rod is rotated to relieve pressure from the golf ball;

said compression assembly comprising a handle bar, said handle bar being coupled to said compression rod opposite said engaging end of said compression rod, said handle bar being adapted for being griped by the user for rotating said compression rod;

said measuring assembly comprising a measuring rod, said measuring rod extending through a measuring aperture of said housing such that a distal end of said measuring rod is positioned in said orifice of said housing, said distal end of said measuring rod being adapted for engaging the golf ball when the golf ball is positioned in said orifice of said housing;

said measuring assembly comprising a measuring biasing member, said measuring biasing member being positioned between said housing and said measuring rod, said measuring biasing member being for biasing said distal end of said measuring rod away from said orifice of said housing;

said measuring assembly comprising a scale means for measuring an amount of pressure applied to the golf ball by said compression assembly, said scale means being operationally coupled to said measuring rod opposite said distal end of said measuring rod such that said scale means detects the amount of movement of said measuring rod when the golf ball is being compressed by said compression assembly; and a display member being coupled to said housing, said display member being operationally coupled to said scale means, said display member being for displaying the pressure the golf ball is applying to said measuring rod.

* * * * *